US012729389B2

(12) United States Patent
Kim et al.

(10) Patent No.: US 12,729,389 B2
(45) Date of Patent: Sep. 8, 2026

(54) MUTANT OF CORYNEBACTERIUM GLUTAMICUM WITH ENHANCED L-LYSINE PRODUCTIVITY AND METHOD FOR PREPARING L-LYSINE USING THE SAME

(71) Applicant: DAESANG CORPORATION, Seoul (KR)

(72) Inventors: Ha Eun Kim, Ulsan (KR); Sun Hee Lee, Gyeonggi-do (KR); Young Ju Lee, Seoul (KR); Seok Hyun Park, Gyeonggi-do (KR); Joon Hyun Park, Gyeonggi-do (KR)

(73) Assignee: DAESANG CORPORATION, Seoul (KR)

( * ) Notice: Subject to any disclaimer, the term of this patent is extended or adjusted under 35 U.S.C. 154(b) by 364 days.

(21) Appl. No.: 18/280,629

(22) PCT Filed: Apr. 26, 2021

(86) PCT No.: PCT/KR2021/005266
§ 371 (c)(1),
(2) Date: Sep. 6, 2023

(87) PCT Pub. No.: WO2022/191357
PCT Pub. Date: Sep. 15, 2022

(65) Prior Publication Data

US 2024/0175064 A1 May 30, 2024

(30) Foreign Application Priority Data

Mar. 9, 2021 (KR) ........................ 10-2021-0030736
Apr. 21, 2021 (KR) ........................ 10-2021-0051472

(51) Int. Cl.

| | |
|---|---|
| ***C12P 13/08*** | (2006.01) |
| ***C12N 1/20*** | (2026.01) |
| ***C12N 9/02*** | (2006.01) |
| ***C12N 15/77*** | (2006.01) |
| ***C12R 1/15*** | (2006.01) |

(52) U.S. Cl.
CPC ................ *C12P 13/08* (2013.01); *C12N 1/20* (2013.01); *C12N 9/0008* (2013.01); *C12N 15/77* (2013.01); *C12R 2001/15* (2021.05); *C12Y 102/01011* (2013.01)

(58) Field of Classification Search
None
See application file for complete search history.

(56) References Cited

U.S. PATENT DOCUMENTS 6,927,046 B1 8/2005 Hanke et al.
9,109,242 B2 * 8/2015 Park ..................... C12N 9/1096

FOREIGN PATENT DOCUMENTS

| | | | |
|---|---|---|---|
| JP | 2020-520645 | 7/2020 | |
| KR | 10-2008-0025355 | 3/2008 | |
| KR | 10-0838038 | 6/2008 | |
| KR | 10-2009-0082702 | 7/2009 | |
| KR | 10-2009-0107665 | 10/2009 | |
| KR | 10-2020-0026881 | 3/2020 | |
| KR | 10-2139806 | 7/2020 | |
| WO | WO-2017085241 A1 * | 5/2017 | ............. C12N 15/52 |

OTHER PUBLICATIONS

Becker et al. From zero to hero—design-based systems metabolic engineering of Corynebacterium glutamicum for L-lysine production. Metab Eng. Mar. 2011;13(2):159-68. (Year: 2011).*
Wu et al. Efficient mining of natural NADH-utilizing dehydrogenases enables systematic cofactor engineering of lysine synthesis pathway of Corynebacterium glutamicum. Metab Eng. Mar. 2019;52:77-86. (Year: 2019).*
Kjeldsen, K. R. (2009). Optimization of an industrial L-lysine producing Corynebacterium glutamicum strain. Technical University of Denmark. (Year: 2009).*
International Search Report issued Dec. 6, 2021 in International (PCT) Application No. PCT/KR2021/005266.
NCBI. Genbank accession No. WP_01113506.1 (May 25, 2020).
Office Action issued Oct. 28, 2024 in Japanese Patent Application No. 2023-555377, with English-language Translation.

* cited by examiner

*Primary Examiner* — Thomas J. Visone
*Assistant Examiner* — Georgiana C Reglas
(74) *Attorney, Agent, or Firm* — Wenderoth, Lind & Ponack, L.L.P.

(57) ABSTRACT

The present disclosure relates to a *Corynebacterium glutamicum* mutant strain having enhanced L-lysine productivity and a method of producing L-lysine using the same. The mutant strain may produce L-lysine in an improved yield compared to the parent strain by increasing or enhancing the expression of a gene encoding aspartate-semialdehyde dehydrogenase therein.

3 Claims, 2 Drawing Sheets

Specification includes a Sequence Listing.

MUTANT OF CORYNEBACTERIUM GLUTAMICUM WITH ENHANCED L-LYSINE PRODUCTIVITY AND METHOD FOR PREPARING L-LYSINE USING THE SAME

SEQUENCE LISTING

A sequence listing in electronic (ASCII text file) format is filed with this application and incorporated herein by reference. The name of the ASCII text file is "Sequence_Listing.txt"; the file was created on Sep. 6, 2023; the size of the file is 15,909 bytes.

BACKGROUND

1. Technical Field

The present disclosure relates to a *Corynebacterium glutamicum* mutant strain having enhanced L-lysine productivity and a method of producing L-lysine using the same.

2. Related Art

L-lysine is an essential amino acid that is not synthesized in the human or animal body. L-lysine needs to be supplied externally and is generally produced by fermentation using microorganisms such as bacteria or yeast. L-lysine production may be performed using naturally occurring wild-type strains or mutant strains obtained by modifying the wild-type strains to have enhanced L-lysine productivity. In recent years, in order to improve the production efficiency of L-lysine, various recombinant strains or mutant strains having excellent L-lysine productivity and methods of producing L-lysine using the same have been developed by applying gene recombination technology to microorganisms such as *Escherichia coli* and *Corynebacterium*, which are widely used for the production of L-amino acids and other useful substances.

According to Korean Patent Nos. 10-0838038 and 10-2139806, L-lysine productivity may be enhanced by increasing the expression of genes encoding proteins, including L-lysine production-related enzymes, through modification of the nucleotide sequences of the genes or the amino acid sequences of the proteins, or by removing unnecessary genes. In addition, Korean Patent Application Publication No. 10-2020-0026881 discloses a method by which the existing promoter of a gene encoding an enzyme involved in L-lysine production is changed to a promoter having strong activity in order to increase the expression of the gene.

As described above, various methods for increasing L-lysine productivity have been developed, but there are dozens of types of proteins such as enzymes, transcription factors, and transport proteins, which are directly or indirectly involved in L-lysine production. Hence, extensive studies still need to be conducted on whether or not changes in the activities of these proteins lead to an increase in L-lysine productivity.

PRIOR ART DOCUMENTS

Patent Documents

Korean Patent No. 10-0838038

Korean Patent No. 10-2139806

Korean Patent Application Publication No. 10-2020-0026881

SUMMARY

An object of the present disclosure is to provide a *Corynebacterium glutamicum* mutant strain having enhanced L-lysine productivity.

Another object of the present disclosure is to provide a method of producing L-lysine using the mutant strain.

The present inventors have conducted studies to develop a novel mutant strain having enhanced L-lysine productivity using a *Corynebacterium glutamicum* strain, and as a result, have found that, when an amino acid at a specific position in the amino acid sequence of the asd gene encoding aspartate-semialdehyde dehydrogenase involved in the L-lysine biosynthesis pathway is substituted, the amount of L-lysine produced increases, thereby completing the present disclosure.

One aspect of the present disclosure provides a *Corynebacterium glutamicum* mutant strain having enhanced L-lysine productivity due to enhanced activity of aspartate-semialdehyde dehydrogenase.

As used herein, the term "aspartate-semialdehyde dehydrogenase" refers to an enzyme involved in step 3 of the L-lysine biosynthesis pathway, which is an enzyme that catalyzes a reaction that produces aspartate 4-semialdehyde from 4-aspartyl phosphate using NADPH.

According to one embodiment of the present disclosure, the aspartate-semialdehyde dehydrogenase may be derived from a strain of the genus *Corynebacterium*. Specifically, the strain of the genus *Corynebacterium* may be *Corynebacterium glutamicum, Corynebacterium crudilactis, Corynebacterium deserti, Corynebacterium callunae, Corynebacterium suranareeae, Corynebacterium lubricantis, Corynebacterium doosanense, Corynebacterium efficiens, Corynebacterium uterequi, Corynebacterium stationis, Corynebacterium pacaense, Corynebacterium singulare, Corynebacterium humireducens, Corynebacterium marinum, Corynebacterium halotolerans, Corynebacterium spheniscorum, Corynebacterium freiburgense, Corynebacterium striatum, Corynebacterium canis, Corynebacterium ammoniagenes, Corynebacterium renale, Corynebacterium pollutisoli, Corynebacterium imitans, Corynebacterium caspium, Corynebacterium testudinoris, Corynebacaterium pseudopelargi*, or *Corynebacterium flavescens*, but is not limited thereto.

As used herein, the "enhanced activity" means that the expression of a gene encoding a protein such as a targeted enzyme, transcription factor or transport protein is newly introduced or increased, so that the expression level of the gene is increased compared to that in the wild-type strain or the strain before modification. The term "enhanced activity" also includes: a case in which the activity of the protein itself is increased compared to the activity of the protein of the original microorganism by substitution, insertion, deletion, or a combination thereof of one or more of the nucleotides encoding the gene; a case in which the overall enzyme activity in the cell is higher than that in the wild-type strain or the strain before modification due to increased expression or translation of the gene encoding the protein; and a combination thereof.

According to one embodiment of the present disclosure, the enhanced activity of the aspartate-semialdehyde dehydrogenase may be achieved by site-directed mutagenesis of the gene encoding the aspartate-semialdehyde dehydrogenase.

According to one embodiment of the present disclosure, the gene encoding the aspartate-semialdehyde dehydrogenase may be represented by the amino acid sequence of SEQ ID NO: 1 or the nucleotide sequence of SEQ ID NO: 2.

According to an embodiment of the present disclosure, the enhanced activity of the aspartate-semialdehyde dehydrogenase may be achieved by substitution of one or more amino acids in the $10^{th}$ to $100^{th}$ amino acid region in the amino acid sequence of the gene encoding the aspartate-semialdehyde dehydrogenase.

More specifically, the genetic mutation in the present disclosure may be achieved by substitution of one or more amino acids in the $10^{th}$ to $100^{th}$ amino acid region, preferably substitution of 1, 2, 3, 4, or 5 consecutive or non-consecutive amino acids in the $20^{th}$ to $100^{th}$, $30^{th}$ to $80^{th}$, $30^{th}$ to $50^{th}$, or $60^{th}$ to $80^{th}$ amino acid region.

In one example of the present disclosure, a *Corynebacterium glutamicum* mutant strain having a new amino acid sequence of the asd gene was obtained by alanine (Ala)-to-glycine (Gly) substitution at position 35, serine (Ser)-to-glutamic acid (Glu) substitution at position 39, and alanine (Ala)-to-valine (Val) substitution at position 78 in the amino acid sequence of the asd gene encoding the aspartate-semialdehyde dehydrogenase of the *Corynebacterium glutamicum* strain. This *Corynebacterium glutamicum* mutant strain may comprise the asd gene represented by the amino acid sequence of SEQ ID NO: 3.

In another example of the present disclosure, a *Corynebacterium glutamicum* mutant strain having a new amino acid sequence of the asd gene was obtained by alanine (Ala)-to-glycine (Gly) substitution at position 35, arginine (Arg)-to-leucine (Ile) substitution at position 38, serine (Ser)-to-glutamic acid (Glu) substitution at position 39, and alanine (Ala)-to valine (Val) substitution at position 78 in the amino acid sequence of the asd gene encoding the aspartate-semialdehyde dehydrogenase of the *Corynebacterium glutamicum* strain. This *Corynebacterium glutamicum* mutant strain may comprise the asd gene represented by the amino acid sequence of SEQ ID NO: 5.

As used herein, the term "enhanced productivity" means that L-lysine productivity of the mutant strain is higher than that of the parent strain. The parent strain refers to a wild-type strain or mutant strain to be mutated, and includes a strain that is to be mutated directly or to be transformed with a recombinant vector or the like. In the present disclosure, the parent strain may be a wild-type *Corynebacterium glutamicum* strain or a strain mutated from the wild-type strain.

According to one embodiment of the present disclosure, the parent strain may be a mutant strain having mutations in the sequences of genes (e.g., lysC, zwf and hom genes) that are involved in lysine production. Specifically, the parent strain may be a *Corynebacterium glutamicum* strain (hereinafter referred to as '*Corynebacterium glutamicum* DS1 strain') deposited with the Korean Culture Center of Microorganisms on Apr. 2, 2021 under accession number KCCM12969P.

In one example of the present disclosure, the *Corynebacterium glutamicum* mutant strain having enhanced L-lysine productivity may contain mutations in the amino acid sequence of the asd gene encoding the aspartate-semialdehyde dehydrogenase, and thus may exhibit increased L-lysine productivity compared to the parent strain. In particular, the *Corynebacterium glutamicum* mutant strain may show an increase in L-lysine production of 3% or more, specifically 3 to 40%, more specifically 5 to 30%, compared to the parent strain, and thus produce 65 to 90 g, preferably 67 to 80 g of L-lysine, per liter of the strain culture medium.

The *Corynebacterium glutamicum* mutant strain according to one embodiment of the present disclosure may recombinant vector comprising a be obtained through variant resulting from substitution of some amino acids in the amino acid sequence of the gene encoding the aspartate-semialdehyde dehydrogenase of the parent strain.

As used herein, the term "some amino acids" means not all of the amino acid sequence, the nucleotide sequence, or the polynucleotide sequence, and may be 1 to 300, preferably 1 to 100, more preferably 1 to 50 amino acids, but is not limited thereto.

As used herein, the term "variant" refers to a variant resulting from substitution of one or more amino acids in the $10^{th}$ to $100^{th}$ amino acid region in the amino acid sequence of the aspartate-semialdehyde dehydrogenase gene that is involved in the biosynthesis of L-lysine.

According to one embodiment of the present disclosure, a variant resulting from substitution of the amino acids at positions 35, 39 and 78 in the amino acid sequence of the aspartate-semialdehyde dehydrogenase gene may have the amino acid sequence of SEQ ID NO: 3 or the nucleotide sequence of SEQ ID NO: 4.

According to one embodiment of the present disclosure, a variant resulting from substitution of the amino acids at positions 35, 38, 39 and 78 in the amino acid sequence of the aspartate-semialdehyde dehydrogenase gene may have the amino acid sequence of SEQ ID NO: 5 or the nucleotide sequence of SEQ ID NO: 6.

As used herein, the term "vector" refers to an expression vector capable of expressing a protein of interest in a suitable host cell, and means a gene construct that contains essential control elements operably linked so that an inserted gene is expressed. As used herein, the term "operably linked" means that a gene to be expressed and the regulatory sequence thereof are functionally linked to each other in a manner enabling gene expression. The term "regulatory elements" includes a promoter for initiating transcription, any operator sequence for controlling transcription, a sequence encoding suitable mRNA ribosome binding sites, and a sequence for controlling termination of transcription and translation. Examples of this vector include, but are not limited to, plasmid vectors, cosmid vectors, bacteriophage vectors, and viral vectors.

As used herein, the term "recombinant vector" may be transformed into a suitable host cell, and then may replicate regardless of the genome of the host cell or may be integrated into the genome itself. In this case, the "suitable host cell" may contain a replication origin, which is a particular nucleotide sequence which enables the vector to replicate in the suitable host cell and from which replication starts.

The transformation may be performed using a suitable vector introduction technique selected depending on the host cell, so that the targeted gene may be expressed in the host cell. For example, introduction of the vector may be performed by electroporation, heat-shock, calcium phosphate ($CaPO_4$) precipitation, calcium chloride ($CaCl_2$) precipitation, microinjection, polyethylene glycol (PEG) method, DEAE-dextran method, cationic liposome method, lithium acetate-DMSO method, or a combination thereof. For the transformed gene, it does not matter whether the gene is inserted into the chromosome of the host cell or located outside of the chromosome, as long as the gene may be expressed in the host cell.

The host cell may include a cell transfected, transformed, or infected with the recombinant vector or polynucleotide of the present disclosure in vivo or in vitro. The host cell containing the recombinant vector of the present disclosure may be a recombinant host cell, a recombinant cell, or a recombinant microorganism.

In addition, the recombinant vector according to the present disclosure may contain a selection marker. The selection marker may be used to select a transformant (host cell) obtained by transformation with the vector. Since only cells expressing the selection marker may survive in the medium treated with the selection marker, the selection marker may select the transformed cells. Representative examples of the selection marker include, but are not limited to, kanamycin, streptomycin, and chloramphenicol.

Genes inserted into the recombinant vector for transformation according to the present disclosure may be substituted into a host cell such as a microorganism of the genus *Corynebacterium* by homologous recombination crossover.

According to one embodiment of the present disclosure, the host cell may be a strain of the genus *Corynebacterium*, for example, a *Corynebacterium glutamicum* DS1 strain.

Another aspect of the present disclosure provides a method for producing L-lysine, the method including steps of: a) culturing the *Corynebacterium glutamicum* mutant strain in a medium; and b) recovering L-lysine from the mutant strain or the medium in which the mutant strain has been cultured.

The culturing may be performed using a suitable medium and culture conditions known in the art, and any person skilled in the art may easily adjust and use the medium and the culture conditions. Specifically, the medium may be a liquid medium, but is not limited thereto. Examples of the culturing method include, but are not limited to, batch culture, continuous culture, fed-batch culture, or a combination thereof.

According to one embodiment of the present disclosure, the medium should meet the requirements of a specific strain in a proper manner, and may be appropriately modified by a person skilled in the art. For the culture medium for the strain of the genus *Corynebacterium*, reference may be made to a known document (Manual of Methods for General Bacteriology, American Society for Bacteriology, Washington D.C., USA, 1981), but is not limited thereto.

According to one embodiment of the present disclosure, the medium may contain various carbon sources, nitrogen sources, and trace element components. Examples of the carbon sources that may be used include: saccharides and carbohydrates such as glucose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol, and organic acids such as acetic acid. These substances may be used individually or as a mixture, but are not limited thereto. Examples of the nitrogen sources that may be used include compounds containing organic nitrogen such as peptone, yeast extract, meat extract, malt extract, corn steep liquor, soybean meal, and urea, or inorganic compounds such as ammonium sulfate, ammonium chloride, ammonium phosphate, ammonium carbonate, and ammonium nitrate. The nitrogen sources may also be used individually or as a mixture, but are not limited thereto. Examples of phosphorus sources that may be used include, but are not limited to, potassium dihydrogen phosphate or dipotassium hydrogen phosphate or the corresponding sodium salts. In addition, the culture medium may contain, but is not limited to, metal salts such as magnesium sulfate or iron sulfate, which are required for growth. In addition, the culture medium may contain essential growth substances such as amino acids and vitamins. Moreover, suitable precursors may be added to the culture medium. The medium or individual components may be added to the culture medium batchwise or in a continuous manner by a suitable method during culturing, but are not limited thereto.

According to one embodiment of the present disclosure, the pH of the culture medium may be adjusted by adding compounds such as ammonium hydroxide, potassium hydroxide, ammonia, phosphoric acid and sulfuric acid to the microorganism culture medium in an appropriate manner during the culturing. In addition, during the culturing, foaming may be suppressed using an anti-foaming agent such as a fatty acid polyglycol ester. Additionally, to keep the culture medium in an aerobic condition, oxygen or an oxygen-containing gas (for example, air) may be injected into the culture medium. The temperature of the culture medium may be generally 20° C. to 45° C., for example, 25° C. to 40° C. The culturing may be continued until a desired amount of L-lysine is produced. Specifically, the culturing time may be 10 hours to 160 hours.

According to one embodiment of the present disclosure, in the step of recovering L-lysine from the cultured mutant strain or the medium in which the mutant strain has been cultured, the produced L-lysine may be collected or recovered from the medium using a suitable method known in the art depending on the culture method. Examples of the method include, but are not limited to, centrifugation, filtration, extraction, spraying, drying, evaporation, precipitation, crystallization, electrophoresis, fractional dissolution (e.g., ammonium sulfate precipitation), chromatography (e.g., ion exchange, affinity, hydrophobicity and size exclusion).

According to one embodiment of the present disclosure, the step of recovering L-lysine may be performed by centrifuging the culture medium at a low speed to remove biomass and separating the obtained supernatant through ion-exchange chromatography.

According to one embodiment of the present disclosure, the step of recovering L-lysine may include a process of purifying L-lysine.

DETAILED DESCRIPTION

Hereinafter, the present disclosure will be described in more detail. However, this description is provided by way of example only to aid the understanding of the present disclosure, and the scope of the present disclosure is not limited by this illustrative description.

Example 1. Construction of *Corynebacterium glutamicum* Mutant Strain

To construct a *Corynebacterium glutamicum* mutant strain having an enhanced activity of aspartate-semialdehyde dehydrogenase, a *Corynebacterium glutamicum* DS1 strain and *E. coli* DH5a (HIT Competent Cells™, Cat No. RH618) were used.

The *Corynebacterium glutamicum* DS1 was cultured in a CM-broth medium (pH 6.8) containing, per liter of distilled water, 5 g of glucose, 2.5 g of NaCl, 5.0 g of yeast extract, 1.0 g of urea, 10.0 g of polypeptone and 5.0 g of beef extract at a temperature of 30° C.

The *E. coli* DH5a was cultured in an LB medium containing, per liter of distilled water, 10.0 g of tryptone, 10.0 g of NaCl and 5.0 g of yeast extract at a temperature of 37° C.

The antibiotics kanamycin and streptomycin used were purchased from Sigma, and DNA sequencing was performed by Macrogen.

1-1. Construction of Recombinant Vector

Figure 1:
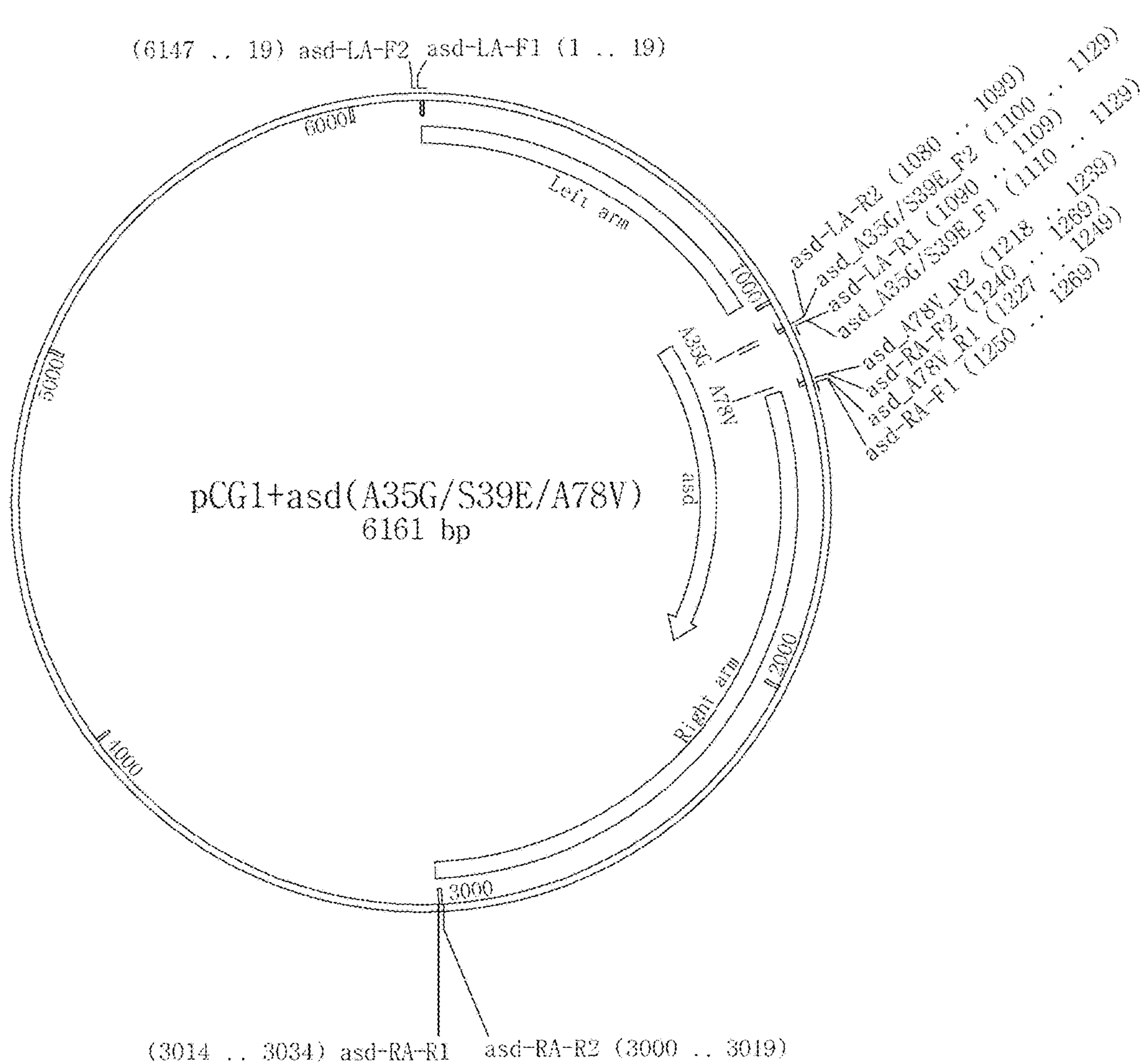
FIG. 1 shows the structure of a pCGI (asd A35G/S39E/A78V) vector containing an asd gene obtained by alanine-to-glycine substitution at amino acid position 35, serine-to-glutamic acid substitution at amino acid position 39, and alanine-to-valine substitution at amino acid position 78 in the amino acid sequence of the asd gene according to one example of the present disclosure.

In order to increase lysine productivity by enhancing the activity of aspartate-semialdehyde dehydrogenase involved in the lysine biosynthesis pathway in the strain, the enhancement of the aspartate-semialdehyde dehydrogenase was introduced. In the method used in this Example, specific mutations in the asd gene were induced in order to increase the expression of the asd gene encoding aspartate-semialdehyde dehydrogenase. Alanine-to-glycine substitution at amino acid position 35, serine-to-glutamic acid substitution at amino acid position 39, and alanine-to-valine substitution at amino acid position 78 in the amino acid sequence of the asd gene were performed, and a 1000-bp region of the left arm and a 1785-bp region of the right arm with respect to the region including 35$^{th}$, 39$^{th}$ and 78$^{th}$ amino acids of the asd gene on the *Corynebacterium glutamicum* genome were amplified by PCR, ligated by overlap PCR, and then cloned into the recombinant vector pCGI (see Kim et al., Journal of Microbiological Methods 84 (2011), 128-130). The resulting plasmid was named pCGI (asdA35G/S39E/A78V) (see FIG. 1). For construction of the plasmid, the primers shown in Table 1 below were used to amplify each gene fragment.

TABLE 1

| | | Primer | SEQ ID NO |
|---|---|---|---|
| Primers for amplification of left homology arm of asd | asd-LA-F1 | 5'-gctctcaggctggtgtgct-3' | 7 |
| | asd-LA-F2 | 5'-gaccatgattacgccgctctcaggctggtgtgct-3' | 8 |
| | asd-LA-R1 | 5'-GGGAACCAAAGAAACGAACA-3' | 9 |
| | asd-LA-R2 | 5'-GAAACGAACAGTGTCAGCTG-3' | 10 |
| Primers for amplification of right homology arm of asd | asd-RA-F1 | 5'-CCACTGTTCGCTGCTGCAGG-3' | 11 |
| | asd-RA-F2 | 5'-GCAGTACGCTCCACTGTTCGCTGCTGCAGG-3' | 12 |
| | asd-RA-R1 | 5'-gatagccgacccgatggccct-3' | 13 |
| | asd-RA-R2 | 5'-ggcccttattcttggaatca-3' | 14 |

PCR was performed using the above primers under the following conditions. Using a thermocycler (TP600, TAKARA BIO Inc., Japan), a reaction solution containing 100 μM of each deoxynucleotide triphosphate (dATP, dCTP, dGTP, dTTP), 1 pM of oligonucleotide, and 10 ng of the chromosomal DNA of the *Corynebacterium glutamicum* DS1 strain as a template, PCR was performed for 30 cycles in the presence of 1 unit of a pfu-x DNA polymerase mixture (Solgent). The PCR was performed for 30 cycles, each consisting of (i) denaturation at 94° C. for 30 sec, (ii) annealing at 58° C. for 30 sec, and (iii) extension at 72° C. for 1 to 2 min (a polymerization time of 2 min per kb).

The gene fragments produced as described above were cloned into the pCGI vector by self-assembly cloning. The vector was transformed into *E. coli* DH5a, which was then streaked on an LB-agar plate containing 50 μg/ml of kanamycin, and cultured at 37° C. for 24 hours. The finally formed colonies were isolated and whether the inserts would be exactly present in the vector was examined, and then the vector was isolated and used for recombination of the *Corynebacterium glutamicum* strain.

As the process commonly performed in the above method, the genes of interest was amplified from the genomic DNA of *Corynebacterium glutamicum* ATCC 13032 genomic DNA by PCR and inserted into the pCGI vector by self-assembly cloning according to the strategy, followed by selection in *E. coli* DH5a. For chromosomal base substitution, the gene fragments were amplified individually and ligated by overlap PCR to obtain a target DNA fragment. During genetic manipulation, Ex Taq polymerase (Takara) and Pfu polymerase (Solgent) were used PCR amplification enzymes, and various restriction enzymes and DNA modifying enzymes used were purchased from NEB. These polymerases and enzymes were used according to the supplied buffer and protocols.

1-2. Construction of Mutant Strain

A DS4 strain, a mutant strain, was constructed using the pCGI (asd A35G/S39E/A78V) vector. The vector was prepared at a final concentration of 1 μg/μl or higher, and introduced into the *Corynebacterium glutamicum* DS1 strain by electroporation (see Tauch et al., FEMS Microbiology Letters 123 (1994), 343-347), thus inducing primary recombination. At this time, the electroporated strain was plated on a CM-agar plate containing 20 μg/μl of kanamycin, and the colonies were isolated, and then whether the vector would properly inserted into the induced position on the genome was analyzed by PCR and sequencing. In order to induce secondary recombination of the isolated strain, the isolated strain was inoculated on a CM-agar liquid medium containing streptomycin, cultured overnight, and then plated on an agar medium containing streptomycin at the same concentration, and the colonies were isolated. Whether the final isolated colonies would have resistance to kanamycin was examined, and then whether mutations were introduced into the asd gene in the strains having no antibiotic resistance was analyzed by sequencing (see Schafer et al., Gene 145

(1994), 69-73). Finally, a *Corynebacterium glutamicum* mutant strain (DS4) having the mutant asd gene introduced therein was obtained.

Example 2. Construction of *Corynebacterium glutamicum* Mutant Strain

A *Corynebacterium glutamicum* mutant strain was constructed in the same manner as in Example 1, except that alanine-to-glycine substitution at amino acid position 35, arginine-to-leucine substitution at amino acid position 38, serine-to-glutamic acid substitution at amino acid position 39, and alanine-to valine substitution at amino acid position 78 in the amino acid sequence of the asd gene were performed.

Figure 2:
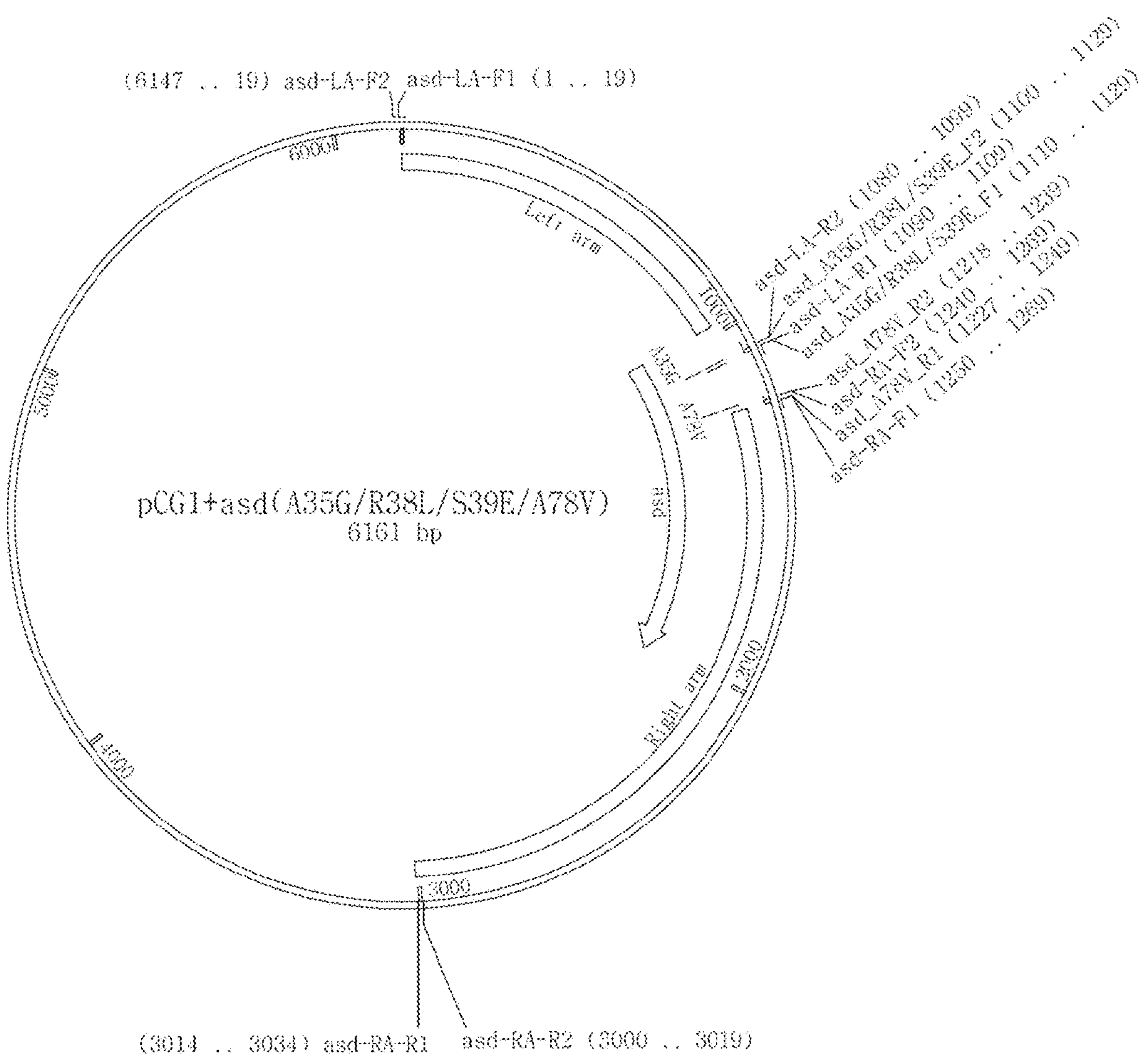
FIG. 2 shows the structure of a pCGI (asd A35G/R38L/S39E/A78V) vector containing an asd gene obtained by alanine-to-glycine substitution at amino acid position 35, arginine-to-leucine substitution at amino acid position 38, serine-to-glutamic acid substitution at amino acid position 39, and alanine-to valine substitution at amino acid position 78 in the amino acid sequence of the asd gene according to one example of the present disclosure.

In this Example, for construction of a plasmid, the primers shown in Table 1 above were used to amplify each gene fragment. A DS4-1 strain, a mutant strain, was constructed using the constructed plasmid pCGI (asd A35G/R38L/S39E/A78V) vector (see FIG. 2). Finally, a *Corynebacterium glutamicum* mutant strain (DS4-1) having the mutant asd gene introduced therein was obtained.

Experimental Example 1. Comparison of L-Lysine Productivity Between Mutant Strains L-lysine productivity was compared between the parent strain *Corynebacterium glutamicum* DS1 strain and the lysine-producing mutant strains DS4 and DS4-1 strains constructed in Examples 1 and 2.

Each of the strains was inoculated into a 100-ml flask containing 10 ml of a lysine medium having the composition shown in Table 2 below, and then cultured with shaking at 180 rpm at 30° C. for 48 hours. After completion of the culture, the amount of L-lysine produced was measured by HPLC (Shimazu, Japan), and the results of the measurement are shown in Table 3 below.

TABLE 2

| Composition | Content (per L of distilled water) |
|---|---|
| Glucose | 100 g |
| Ammonium sulfate | 55 g |
| $(NH_4)_2SO_4$ | 35 g |
| $KH_2PO_4$ | 1.1 g |
| $MgSO_4•H_2O$ | 1.2 g |
| $MnSO_4•H_2O$ | 180 mg |
| $FeSO_4•H_2O$ | 180 mg |
| Thiamine•HCl | 9 mg |
| Biotin | 1.8 mg |
| $CaCO_3$ | 5% |
| pH | 7.0 |

TABLE 3

| Strain | $OD_{610}$ | L-lysine (g/L) | L-lysine production per gram dry cell weight (g/gDCW) |
|---|---|---|---|
| Parent strain (DS1) | 22 | 64.8 | 7.0 |
| Mutant strain (DS4) | 22.2 | 71.9 | 7.7 |
| Mutant strain (DS4-1) | 21.6 | 67.4 | 7.4 |

As shown in Table 3 above, it was confirmed that, in the *Corynebacterium glutamicum* mutant strains DS4 and DS4-1 in which specific positions (amino acids at positions 35, 39 and 78, or amino acids at positions 35, 38, 39 and 78) in the amino acid sequence of the asd gene were substituted with optimal amino acids to enhance the lysine biosynthesis pathway, the L-lysine productivities of the mutant strains increased by about 10.0% and 5.7%, respectively, compared to that of the parent strain *Corynebacterium glutamicum* DS1 strain. From these results, it could be seen that enhanced expression of the asd gene enhanced L-lysine productivity of the mutant strain by enhancing the supply of the lysine precursor.

As described above, the *Corynebacterium glutamicum* mutant strain according to the present disclosure may produce L-lysine in an improved yield compared to the parent strain by increasing or enhancing the expression of the gene encoding aspartate-semialdehyde dehydrogenase therein.

So far, the present disclosure has been described with reference to the embodiments thereof. Those of ordinary skill in the art to which the present disclosure pertains will appreciate that the present disclosure may be embodied in modified forms without departing from the essential characteristics of the present disclosure. Therefore, the disclosed embodiments should be considered from an illustrative point of view, not from a restrictive point of view. The scope of the present disclosure is defined by the claims rather than the foregoing description, and all differences within the scope equivalent thereto should be construed as being included in the present disclosure.

What is claimed is:

1. A *Corynebacterium glutamicum* mutant strain having enhanced L-lysine productivity by a substitution of glycine for alanine at position 35, a substitution of glutamic acid for serine at position 39, and a substitution of valine for alanine at position 78; or a substitution of glycine for alanine at position 35, a substitution of leucine for arginine at position 38, a substitution of glutamic acid for serine at position 39, and a substitution of valine for alanine at position 78 in the amino acid sequence of aspartate-semialdehyde dehydrogenase of SEQ ID NO: 1.

2. The *Corynebacterium glutamicum* mutant strain of claim 1, which comprises the amino acid sequence of SEQ ID NO: 3 or 5.

3. A method for producing L-lysine, the method comprising steps of:

a) culturing the mutant strain of claim 1 in a medium; and b) recovering L-lysine from the mutant strain or the medium in which the mutant strain has been cultured.

* * * * *

SEQUENCE LISTING

```
<160> NUMBER OF SEQ ID NOS: 14

<210> SEQ ID NO 1
<211> LENGTH: 344
<212> TYPE: PRT
<213> ORGANISM: Artificial Sequence
<220> FEATURE:
<223> OTHER INFORMATION: Amino acid sequence of asd gene

<400> SEQUENCE: 1

Met Thr Thr Ile Ala Val Val Gly Ala Thr Gly Gln Val Gly Gln Val
1               5                   10                  15

Met Arg Thr Leu Leu Glu Glu Arg Asn Phe Pro Ala Asp Thr Val Arg
            20                  25                  30
```

```
Phe Phe Ala Ser Pro Arg Ser Ala Gly Arg Lys Ile Glu Phe Arg Gly
        35                  40                  45

Thr Glu Ile Glu Val Glu Asp Ile Thr Gln Ala Thr Glu Glu Ser Leu
    50                  55                  60

Lys Asp Ile Asp Val Ala Leu Phe Ser Ala Gly Gly Thr Ala Ser Lys
65                  70                  75                  80

Gln Tyr Ala Pro Leu Phe Ala Ala Ala Gly Ala Thr Val Val Asp Asn
                85                  90                  95

Ser Ser Ala Trp Arg Lys Asp Asp Glu Val Pro Leu Ile Val Ser Glu
            100                 105                 110

Val Asn Pro Ser Asp Lys Asp Ser Leu Val Lys Gly Ile Ile Ala Asn
        115                 120                 125

Pro Asn Cys Thr Thr Met Ala Ala Met Pro Val Leu Lys Pro Leu His
    130                 135                 140

Asp Ala Ala Gly Leu Val Lys Leu His Val Ser Ser Tyr Gln Ala Val
145                 150                 155                 160

Ser Gly Ser Gly Leu Ala Gly Val Glu Thr Leu Ala Lys Gln Val Ala
                165                 170                 175

Ala Val Gly Asp His Asn Val Glu Phe Val His Asp Gly Gln Ala Ala
            180                 185                 190

Asp Ala Gly Asp Val Gly Pro Tyr Val Ser Pro Ile Ala Tyr Asn Val
        195                 200                 205

Leu Pro Phe Ala Gly Asn Leu Val Asp Asp Gly Thr Phe Glu Thr Asp
    210                 215                 220

Glu Glu Gln Lys Leu Arg Asn Glu Ser Arg Lys Ile Leu Gly Leu Pro
225                 230                 235                 240

Asp Leu Lys Val Ser Gly Thr Cys Val Arg Val Pro Val Phe Thr Gly
                245                 250                 255

His Thr Leu Thr Ile His Ala Glu Phe Asp Lys Ala Ile Thr Val Asp
            260                 265                 270

Gln Ala Gln Glu Ile Leu Gly Ala Ala Ser Gly Val Lys Leu Val Asp
        275                 280                 285

Val Pro Thr Pro Leu Ala Ala Ala Gly Ile Asp Glu Ser Leu Val Gly
    290                 295                 300

Arg Ile Arg Gln Asp Ser Thr Val Asp Asp Asn Arg Gly Leu Val Leu
305                 310                 315                 320

Val Val Ser Gly Asp Asn Leu Arg Lys Gly Ala Ala Leu Asn Thr Ile
                325                 330                 335

Gln Ile Ala Glu Leu Leu Val Lys
            340
```

<210> SEQ ID NO 2
<211> LENGTH: 1035
<212> TYPE: DNA
<213> ORGANISM: Artificial Sequence
<220> FEATURE:
<223> OTHER INFORMATION: Polynucleotide sequence of asd gene

<400> SEQUENCE: 2

```
atgaccacca tcgcagttgt tggtgcaacc ggccaggtcg gccaggttat gcgcaccctt      60

ttggaagagc gcaatttccc agctgacact gttcgtttct ttgcttcccc acgttccgca     120

ggccgtaaga ttgaattccg tggcacggaa atcgaggtag aagacattac tcaggcaacc     180

gaggagtccc tcaaggacat cgacgttgcg ttgttctccg ctggaggcac cgcttccaag     240

cagtacgctc cactgttcgc tgctgcaggc gcgactgttg tggataactc ttctgcttgg     300
```

```
cgcaaggacg acgaggttcc actaatcgtc tctgaggtga acccttccga caaggattcc    360

ctggtcaagg gcattattgc gaaccctaac tgcaccacca tggctgcgat gccagtgctg    420

aagccacttc acgatgccgc tggtcttgta aagcttcacg tttcctctta ccaggctgtt    480

tccggttctg gtcttgcagg tgtggaaacc ttggcaaagc aggttgctgc agttggagac    540

cacaacgttg agttcgtcca tgatggacag gctgctgacg caggcgatgt cggaccttat    600

gtttcaccaa tcgcttacaa cgtgctgcca ttcgccggaa acctcgtcga tgacggcacc    660

ttcgaaaccg atgaagagca gaagctgcgc aacgaatccc gcaagattct cggtctccca    720

gacctcaagg tctcaggcac ctgcgtccgc gtgccggttt tcaccggcca cacgctgacc    780

attcacgccg aattcgacaa ggcaatcacc gtggaccagg cgcaggagat cttgggtgcc    840

gcttcaggcg tcaagcttgt cgacgtccca accccacttg cagctgccgg cattgacgaa    900

tccctcgttg gacgcatccg tcaggactcc actgtcgacg ataaccgcgg tctggttctc    960

gtcgtatctg gcgacaacct ccgcaagggt gctgcgctaa acaccatcca gatcgctgag   1020

ctgctggtta agtaa                                                    1035
```

```
<210> SEQ ID NO 3
<211> LENGTH: 344
<212> TYPE: PRT
<213> ORGANISM: Artificial Sequence
<220> FEATURE:
<223> OTHER INFORMATION: Mutant amino acid sequence of asd gene

<400> SEQUENCE: 3

Met Thr Thr Ile Ala Val Val Gly Ala Thr Gly Gln Val Gly Gln Val
1               5                   10                  15

Met Arg Thr Leu Leu Glu Glu Arg Asn Phe Pro Ala Asp Thr Val Arg
            20                  25                  30

Phe Phe Gly Ser Pro Arg Glu Ala Gly Arg Lys Ile Glu Phe Arg Gly
        35                  40                  45

Thr Glu Ile Glu Val Glu Asp Ile Thr Gln Ala Thr Glu Glu Ser Leu
    50                  55                  60

Lys Asp Ile Asp Val Ala Leu Phe Ser Ala Gly Gly Thr Val Ser Lys
65                  70                  75                  80

Gln Tyr Ala Pro Leu Phe Ala Ala Ala Gly Ala Thr Val Val Asp Asn
                85                  90                  95

Ser Ser Ala Trp Arg Lys Asp Asp Glu Val Pro Leu Ile Val Ser Glu
            100                 105                 110

Val Asn Pro Ser Asp Lys Asp Ser Leu Val Lys Gly Ile Ile Ala Asn
        115                 120                 125

Pro Asn Cys Thr Thr Met Ala Ala Met Pro Val Leu Lys Pro Leu His
    130                 135                 140

Asp Ala Ala Gly Leu Val Lys Leu His Val Ser Ser Tyr Gln Ala Val
145                 150                 155                 160

Ser Gly Ser Gly Leu Ala Gly Val Glu Thr Leu Ala Lys Gln Val Ala
                165                 170                 175

Ala Val Gly Asp His Asn Val Glu Phe Val His Asp Gly Gln Ala Ala
            180                 185                 190

Asp Ala Gly Asp Val Gly Pro Tyr Val Ser Pro Ile Ala Tyr Asn Val
        195                 200                 205

Leu Pro Phe Ala Gly Asn Leu Val Asp Asp Gly Thr Phe Glu Thr Asp
    210                 215                 220
```

-continued

```
Glu Glu Gln Lys Leu Arg Asn Glu Ser Arg Lys Ile Leu Gly Leu Pro
225                 230                 235                 240

Asp Leu Lys Val Ser Gly Thr Cys Val Arg Val Pro Val Phe Thr Gly
                245                 250                 255

His Thr Leu Thr Ile His Ala Glu Phe Asp Lys Ala Ile Thr Val Asp
            260                 265                 270

Gln Ala Gln Glu Ile Leu Gly Ala Ala Ser Gly Val Lys Leu Val Asp
        275                 280                 285

Val Pro Thr Pro Leu Ala Ala Ala Gly Ile Asp Glu Ser Leu Val Gly
    290                 295                 300

Arg Ile Arg Gln Asp Ser Thr Val Asp Asp Asn Arg Gly Leu Val Leu
305                 310                 315                 320

Val Val Ser Gly Asp Asn Leu Arg Lys Gly Ala Ala Leu Asn Thr Ile
                325                 330                 335

Gln Ile Ala Glu Leu Leu Val Lys
            340
```

<210> SEQ ID NO 4
<211> LENGTH: 1035
<212> TYPE: DNA
<213> ORGANISM: Artificial Sequence
<220> FEATURE:
<223> OTHER INFORMATION: Mutant polynucleotide sequence of asd gene

<400> SEQUENCE: 4

```
atgaccacca tcgcagttgt tggtgcaacc ggccaggtcg gccaggttat gcgcaccctt     60

ttggaagagc gcaatttccc agctgacact gttcgtttct ttggttcccc acgtgaagca    120

ggccgtaaga ttgaattccg tggcacggaa atcgaggtag aagacattac tcaggcaacc    180

gaggagtccc tcaaggacat cgacgttgcg ttgttctccg ctggaggcac cgtttccaag    240

cagtacgctc cactgttcgc tgctgcaggc gcgactgttg tggataactc ttctgcttgg    300

cgcaaggacg acgaggttcc actaatcgtc tctgaggtga acccttccga caaggattcc    360

ctggtcaagg gcattattgc gaaccctaac tgcaccacca tggctgcgat gccagtgctg    420

aagccacttc acgatgccgc tggtcttgta aagcttcacg tttcctctta ccaggctgtt    480

tccggttctg gtcttgcagg tgtggaaacc ttggcaaagc aggttgctgc agttggagac    540

cacaacgttg agttcgtcca tgatggacag gctgctgacg caggcgatgt cggaccttat    600

gtttcaccaa tcgcttacaa cgtgctgcca ttcgccggaa acctcgtcga tgacggcacc    660

ttcgaaaccg atgaagagca gaagctgcgc aacgaatccc gcaagattct cggtctccca    720

gacctcaagg tctcaggcac ctgcgtccgc gtgccggttt tcaccggcca cacgctgacc    780

attcacgccg aattcgacaa ggcaatcacc gtggaccagg cgcaggagat cttgggtgcc    840

gcttcaggcg tcaagcttgt cgacgtccca accccacttg cagctgccgg cattgacgaa    900

tccctcgttg gacgcatccg tcaggactcc actgtcgacg ataaccgcgg tctggttctc    960

gtcgtatctg gcgacaacct ccgcaagggt gctgcgctaa acaccatcca gatcgctgag   1020

ctgctggtta agtaa                                                    1035
```

<210> SEQ ID NO 5
<211> LENGTH: 344
<212> TYPE: PRT
<213> ORGANISM: Artificial Sequence
<220> FEATURE:
<223> OTHER INFORMATION: Mutant amino acid sequence of asd gene

<400> SEQUENCE: 5

```
Met Thr Thr Ile Ala Val Val Gly Ala Thr Gly Gln Val Gly Gln Val
1               5                   10                  15

Met Arg Thr Leu Leu Glu Glu Arg Asn Phe Pro Ala Asp Thr Val Arg
            20                  25                  30

Phe Phe Gly Ser Pro Leu Glu Ala Gly Arg Lys Ile Glu Phe Arg Gly
        35                  40                  45

Thr Glu Ile Glu Val Glu Asp Ile Thr Gln Ala Thr Glu Glu Ser Leu
    50                  55                  60

Lys Asp Ile Asp Val Ala Leu Phe Ser Ala Gly Gly Thr Val Ser Lys
65                  70                  75                  80

Gln Tyr Ala Pro Leu Phe Ala Ala Ala Gly Ala Thr Val Val Asp Asn
                85                  90                  95

Ser Ser Ala Trp Arg Lys Asp Asp Glu Val Pro Leu Ile Val Ser Glu
            100                 105                 110

Val Asn Pro Ser Asp Lys Asp Ser Leu Val Lys Gly Ile Ile Ala Asn
        115                 120                 125

Pro Asn Cys Thr Thr Met Ala Ala Met Pro Val Leu Lys Pro Leu His
    130                 135                 140

Asp Ala Ala Gly Leu Val Lys Leu His Val Ser Ser Tyr Gln Ala Val
145                 150                 155                 160

Ser Gly Ser Gly Leu Ala Gly Val Glu Thr Leu Ala Lys Gln Val Ala
                165                 170                 175

Ala Val Gly Asp His Asn Val Glu Phe Val His Asp Gly Gln Ala Ala
            180                 185                 190

Asp Ala Gly Asp Val Gly Pro Tyr Val Ser Pro Ile Ala Tyr Asn Val
        195                 200                 205

Leu Pro Phe Ala Gly Asn Leu Val Asp Asp Gly Thr Phe Glu Thr Asp
    210                 215                 220

Glu Glu Gln Lys Leu Arg Asn Glu Ser Arg Lys Ile Leu Gly Leu Pro
225                 230                 235                 240

Asp Leu Lys Val Ser Gly Thr Cys Val Arg Val Pro Val Phe Thr Gly
                245                 250                 255

His Thr Leu Thr Ile His Ala Glu Phe Asp Lys Ala Ile Thr Val Asp
            260                 265                 270

Gln Ala Gln Glu Ile Leu Gly Ala Ala Ser Gly Val Lys Leu Val Asp
        275                 280                 285

Val Pro Thr Pro Leu Ala Ala Ala Gly Ile Asp Glu Ser Leu Val Gly
    290                 295                 300

Arg Ile Arg Gln Asp Ser Thr Val Asp Asp Asn Arg Gly Leu Val Leu
305                 310                 315                 320

Val Val Ser Gly Asp Asn Leu Arg Lys Gly Ala Ala Leu Asn Thr Ile
                325                 330                 335

Gln Ile Ala Glu Leu Leu Val Lys
            340
```

<210> SEQ ID NO 6
<211> LENGTH: 1035
<212> TYPE: DNA
<213> ORGANISM: Artificial Sequence
<220> FEATURE:
<223> OTHER INFORMATION: Mutant polynucleotide sequence of asd gene

<400> SEQUENCE: 6

```
atgaccacca tcgcagttgt tggtgcaacc ggccaggtcg gccaggttat gcgcaccctt      60
```

```
ttggaagagc gcaatttccc agctgacact gttcgtttct ttggttcccc acttgaagca    120

ggccgtaaga ttgaattccg tggcacggaa atcgaggtag aagacattac tcaggcaacc    180

gaggagtccc tcaaggacat cgacgttgcg ttgttctccg ctggaggcac cgtttccaag    240

cagtacgctc cactgttcgc tgctgcaggc gcgactgttg tggataactc ttctgcttgg    300

cgcaaggacg acgaggttcc actaatcgtc tctgaggtga acccttccga caaggattcc    360

ctggtcaagg gcattattgc gaaccctaac tgcaccacca tggctgcgat gccagtgctg    420

aagccacttc acgatgccgc tggtcttgta aagcttcacg tttcctctta ccaggctgtt    480

tccggttctg gtcttgcagg tgtggaaacc ttggcaaagc aggttgctgc agttggagac    540

cacaacgttg agttcgtcca tgatggacag gctgctgacg caggcgatgt cggaccttat    600

gtttcaccaa tcgcttacaa cgtgctgcca ttcgccggaa acctcgtcga tgacggcacc    660

ttcgaaaccg atgaagagca gaagctgcgc aacgaatccc gcaagattct cggtctccca    720

gacctcaagg tctcaggcac ctgcgtccgc gtgccggttt tcaccggcca cacgctgacc    780

attcacgccg aattcgacaa ggcaatcacc gtggaccagg cgcaggagat cttgggtgcc    840

gcttcaggcg tcaagcttgt cgacgtccca accccacttg cagctgccgg cattgacgaa    900

tccctcgttg gacgcatccg tcaggactcc actgtcgacg ataaccgcgg tctggttctc    960

gtcgtatctg gcgacaacct ccgcaagggt gctgcgctaa acaccatcca gatcgctgag   1020

ctgctggtta agtaa                                                    1035
```

<210> SEQ ID NO 7
<211> LENGTH: 19
<212> TYPE: DNA
<213> ORGANISM: Artificial Sequence
<220> FEATURE:
<223> OTHER INFORMATION: chemically-synthesized primer asd-LA-F1

<400> SEQUENCE: 7

```
gctctcaggc tggtgtgct                                                  19
```

<210> SEQ ID NO 8
<211> LENGTH: 34
<212> TYPE: DNA
<213> ORGANISM: Artificial Sequence
<220> FEATURE:
<223> OTHER INFORMATION: chemically-synthesized primer asd-LA-F2

<400> SEQUENCE: 8

```
gaccatgatt acgccgctct caggctggtg tgct                                 34
```

<210> SEQ ID NO 9
<211> LENGTH: 20
<212> TYPE: DNA
<213> ORGANISM: Artificial Sequence
<220> FEATURE:
<223> OTHER INFORMATION: chemically-synthesized primer asd-LA-R1

<400> SEQUENCE: 9

```
gggaaccaaa gaaacgaaca                                                 20
```

<210> SEQ ID NO 10
<211> LENGTH: 20
<212> TYPE: DNA
<213> ORGANISM: Artificial Sequence
<220> FEATURE:
<223> OTHER INFORMATION: chemically-synthesized primer asd-LA-R2

<400> SEQUENCE: 10

-continued

```
gaaacgaaca gtgtcagctg                                                   20


<210> SEQ ID NO 11
<211> LENGTH: 20
<212> TYPE: DNA
<213> ORGANISM: Artificial Sequence
<220> FEATURE:
<223> OTHER INFORMATION: chemically-synthesized primer asd-RA-F1

<400> SEQUENCE: 11

ccactgttcg ctgctgcagg                                                   20


<210> SEQ ID NO 12
<211> LENGTH: 30
<212> TYPE: DNA
<213> ORGANISM: Artificial Sequence
<220> FEATURE:
<223> OTHER INFORMATION: chemically-synthesized primer asd-RA-F2

<400> SEQUENCE: 12

gcagtacgct ccactgttcg ctgctgcagg                                        30


<210> SEQ ID NO 13
<211> LENGTH: 21
<212> TYPE: DNA
<213> ORGANISM: Artificial Sequence
<220> FEATURE:
<223> OTHER INFORMATION: chemically-synthesized primer asd-RA-R1

<400> SEQUENCE: 13

gatagccgac ccgatggccc t                                                 21


<210> SEQ ID NO 14
<211> LENGTH: 20
<212> TYPE: DNA
<213> ORGANISM: Artificial Sequence
<220> FEATURE:
<223> OTHER INFORMATION: chemically-synthesized primer asd-RA-R2

<400> SEQUENCE: 14

ggcccttatt cttggaatca                                                   20
```